United States Patent [19]

Nasser

[11] 4,344,316
[45] Aug. 17, 1982

[54] METHOD AND APPARATUS FOR INDICATING THE AIR CONTENT OF CONCRETE IN SITU

[75] Inventor: Karim W. Nasser, Saskatoon, Canada

[73] Assignee: Canadian Patents & Development Ltd., Ottawa, Canada

[21] Appl. No.: 191,832

[22] Filed: Sep. 29, 1980

[30] Foreign Application Priority Data

Oct. 30, 1979 [CA] Canada ................................ 338752

[51] Int. Cl.³ .......................................... G01N 7/16
[52] U.S. Cl. ................................................. 73/19
[58] Field of Search ................................ 73/19, 23

[56] References Cited

U.S. PATENT DOCUMENTS 2,668,437 2/1954 Patch .................................... 73/19

FOREIGN PATENT DOCUMENTS 697929 11/1979 U.S.S.R. ................................ 73/19

OTHER PUBLICATIONS

C. A. Menzel, "Development and Study of Apparatus and Methods for Determination of Air Content of Fresh Concrete", *Journal Am. Concrete Institute*, vol. 18, No. 9, pp. 1053–1072, May 1947.

Primary Examiner—Stephen A. Kreitman
Attorney, Agent, or Firm—Ronald G. Bitner

[57] ABSTRACT

The apparatus comprises a chamber having an open end and an opposite closeable end, and provided with a heating device and pressure measuring device. The open end of the chamber is inserted into the fresh concrete with opposite end opened. After insertion the chamber is closed and the contents heated under predetermined conditions. The pressure increase is a function of air content of the mixture.

4 Claims, 4 Drawing Figures

METHOD AND APPARATUS FOR INDICATING THE AIR CONTENT OF CONCRETE IN SITU

BACKGROUND OF THE INVENTION

The present invention relates to a method and apparatus for indicating the air content of fresh concrete in situ.

It is common practice to entrain concrete mixes with air in order to resist freeze-thaw cycles and also to improve durability and workability. Since the quantity of entrained air is subject to variation due to a number of factors, and since these variations in air content affect the strength and durability of the concrete, it is important that the air content of a concrete mix be known.

A commonly used method for determining air content involves placing a sample of the concrete mix in a container of known volume, sealing the container, connecting with a pressurized chamber of known pressure and volume, allowing equalization of pressure from the pressurized chamber to the container and measuring the resulting pressure. The resulting pressure drop will be a function to the air content of the container in accordance with Boyle's law.

Although the aforesaid method can accurately determine the air content of a particular sample of concrete mixes, it does not necessarily indicate the air content of the concrete mix placed in situ. Transport and/or placing of the concrete mix subsequent to testing of a sample can reduce the air content significantly, due, for example, to overvibration, lag time and temperature effects. With present testing methods, such a reduction in air content may go undetected until premature deterioration occurs.

SUMMARY OF THE INVENTION

It is an object of the present invention to provide a method and apparatus for indicating the air content of a concrete mix in situ.

It has been found that the air content of fresh concrete placed in situ can be conveniently determined by means of a chamber with one open end and a closeable opposite end and provided with heating means. When the open end is inserted into fresh concrete the chamber encloses a predetermined volume of concrete. When the enclosed volume of concrete is heated, under predetermined conditions, the pressure increase will be a function of the amount of air in the concrete.

More specifically, the present invention comprises a method for indicating the air content of fresh concrete in situ, comprising: providing a chamber having an open end and an opposite closeable end, said chamber provided with heating means and pressure indicating means; inserting the open end of the chamber into the concrete, with opposite end opened; closing the chamber and heating the contents with a predetermined energy input at a temperature less than the boiling point; and determining the pressure increase in the chamber, wherein the pressure increase is a function of the air content.

The apparatus of the present invention comprises: a chamber having an open end and an opposite sealable end having opening means, said open end adapted for insertion into fresh concrete; heating means disposed in the chamber for heating the contents of the chamber; pressure measuring means for connection with the chamber for indicating a pressure increase in the chamber as the result of heating.

DESCRIPTION OF PREFERRED EMBODIMENT

Figure 1:
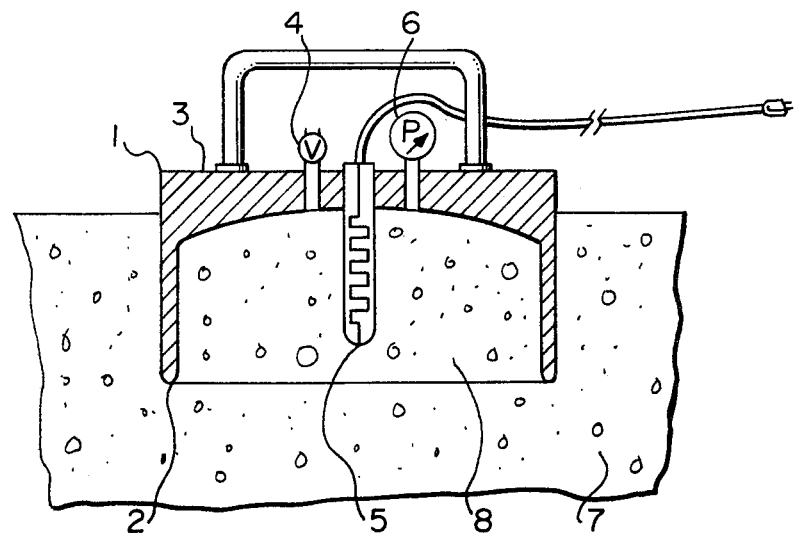
FIG. 1 is a schematic illustration of the apparatus of the present invention in situ.

With reference to FIG. 1, the apparatus of the present invention comprises a chamber 1 having an open end 2 and a sealable end 3. The sealable end of the chamber is provided with venting means in the form of a valve 4. Disposed within the chamber is heating means 5. Connected with the chamber is pressure measuring means 6.

In operation, the open end of the chamber 1 is inserted into the fresh concrete 7, with the venting valve 4 opened. Having the valve open allows air to escape as the device is pushed down so that the chamber will be filled completely with concrete, i.e., without air spaces which could affect accuracy. When the apparatus is inserted fully, as shown in FIG. 1, the valve 4 is closed and heating means 5 is activated.

The contents 8 of the chamber 1 are provided with a predetermined heat energy, for example by energizing a given heating element 5 for a predetermined amount of time. Heating of the contents of the chamber 1 produces a pressure increase that is a function of the air content of the concrete mixture. The pressure increase resulting from a predetermined heat energy input can therefore be calibrated to provide a measure of the air content.

Heating must be limited to avoid boiling of the water in the mixture, since steam generation would produce incorrectly high pressure values.

With the embodiment of FIG. 1, the chamber must be filled completely with concrete after insertion. A chamber with a transparent top will provide a visual indication that this has occurred.

Slight vibration by hand of the chamber while inserting reduces the possibility of air being entrapped in the chamber, particularly around the heater and fins.

After the testing is complete, the valve 4 may again be opened to facilitate withdrawal of the chamber 1.

The pressure increase as a result of heating will tend to lift the chamber. The tendency to lift is resisted by the weight of the chamber and the friction on the walls of the chamber. Such lifting, which would result in incorrectly low pressure values, may be avoided by providing weight sufficient to balance the forces corresponding with the maximum pressure increases that can be expected from the chosen heating schedule.

Figure 2:
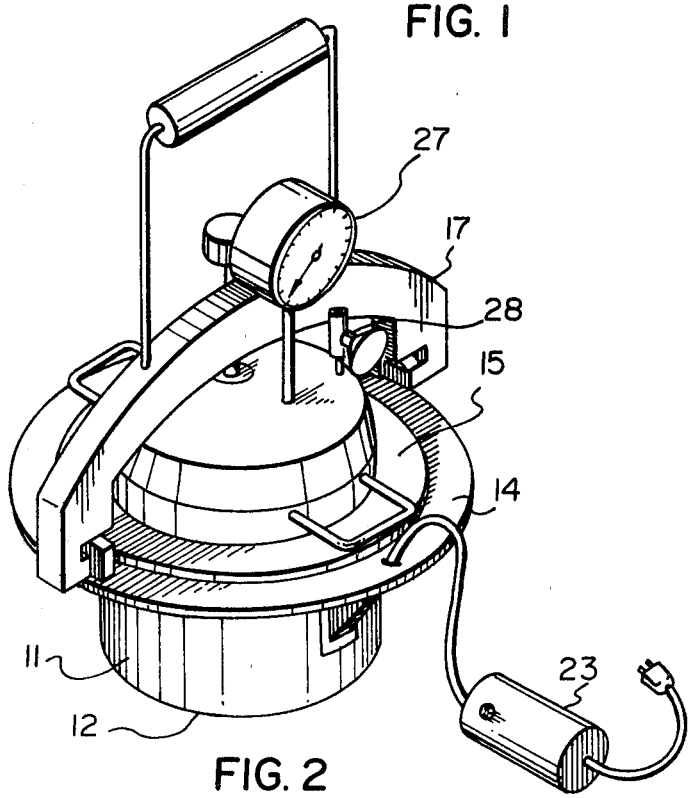
FIG. 2 is a perspective view of one specific embodiment of the apparatus.
Figure 3:
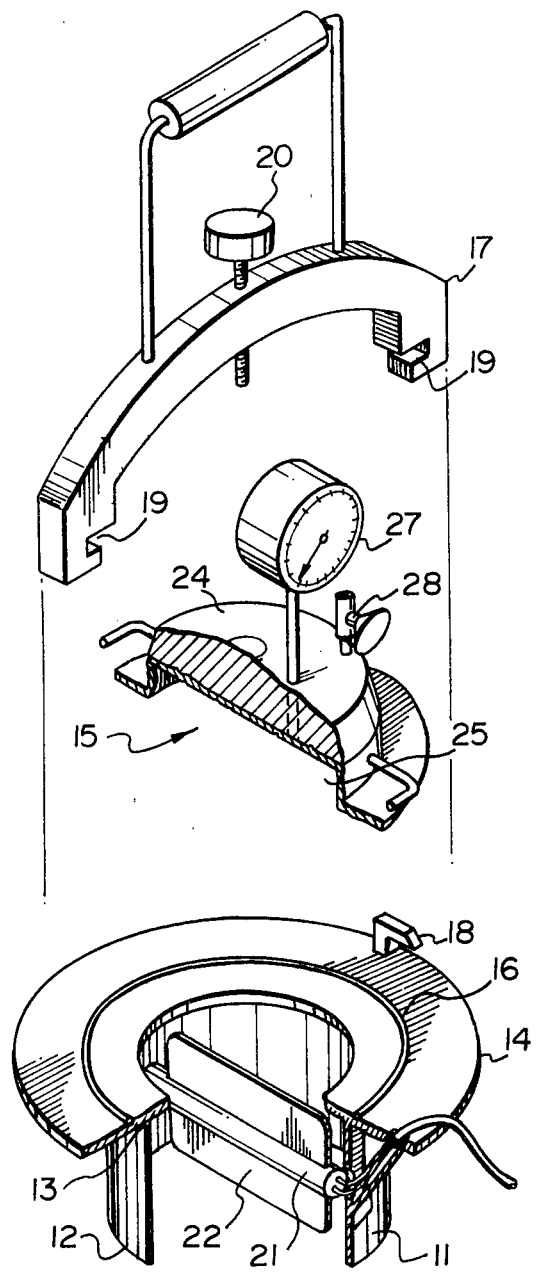
FIG. 3 is a partly fragmented view showing the components of FIG. 2 separated.

FIGS. 2 and 3 illustrate a detailed embodiment of the invention. As in the embodiment of FIG. 1, the chamber 11 has an open end 12 and a sealable end 13. The sealable end 13 includes a flange 14 adapted to be sealingly engaged by a cover plate 15, with sealing facilitated by the use of an O-ring 16. The cover 15 is releasably secured to the tubular chamber by means of a clamping device 17 with mating projections 18 and recesses 19, and screw 20 for tightening the cover against the chamber 11.

Disposed within the chamber 11 is a heating element 21 with vertical fins 22 to increase the surface area. The heating cycle is controlled by a timer 23.

The cover 15 is provided with an additional weight 24 to oppose the tendency to lift, as discussed herein. The cover 15 is shaped to form a space 25, above the flange 14, which prevents concrete from plugging passageways to the pressure gauge 27 and valve 28. The valve 28 allows communication between the cavity 25 and atmosphere.

For testing, the tubular chamber 11, with cover 15 removed, is inserted into the concrete to be tested until the flange 14 rests on the surface of the concrete. The cover 15 is then placed on the flange, with valve 28 opened so that the pressure within the closed chamber will be at atmospheric pressure when heating is initiated, and the clamping element applied as shown in FIG. 2. The valve 28 is then shut and the heating cycle begun using the timer 23 to control duration. When the selected time has elapsed the pressure rise as indicated by the pressure gauge 27 can be used to indicate the air content as in the embodiment of FIG. 1.

EXAMPLE

An apparatus similar to that illustrated in FIGS. 2 and 3 was constructed. The chamber was constructed from a stainless steel pipe 9.5 cm. long, 15 cm. diameter and 0.3 cm. thick, with an annular flange having an outside diameter of 25 cm. and inside opening of 11 cm. The dimensions of the cylindrical cavity defined by the cover was 11 cm. in diameter and 3 cm. in depth. The total weight of the apparatus including additional lead weights on the cover was 11 kg.

The heating element comprised a 1,100 watt, 110 volt cartridge type heater 2 cm. in diameter and 15 cm. in length having copper fins projecting above and below. Tests using this apparatus were performed on concrete of varying air contents.

Figure 4:
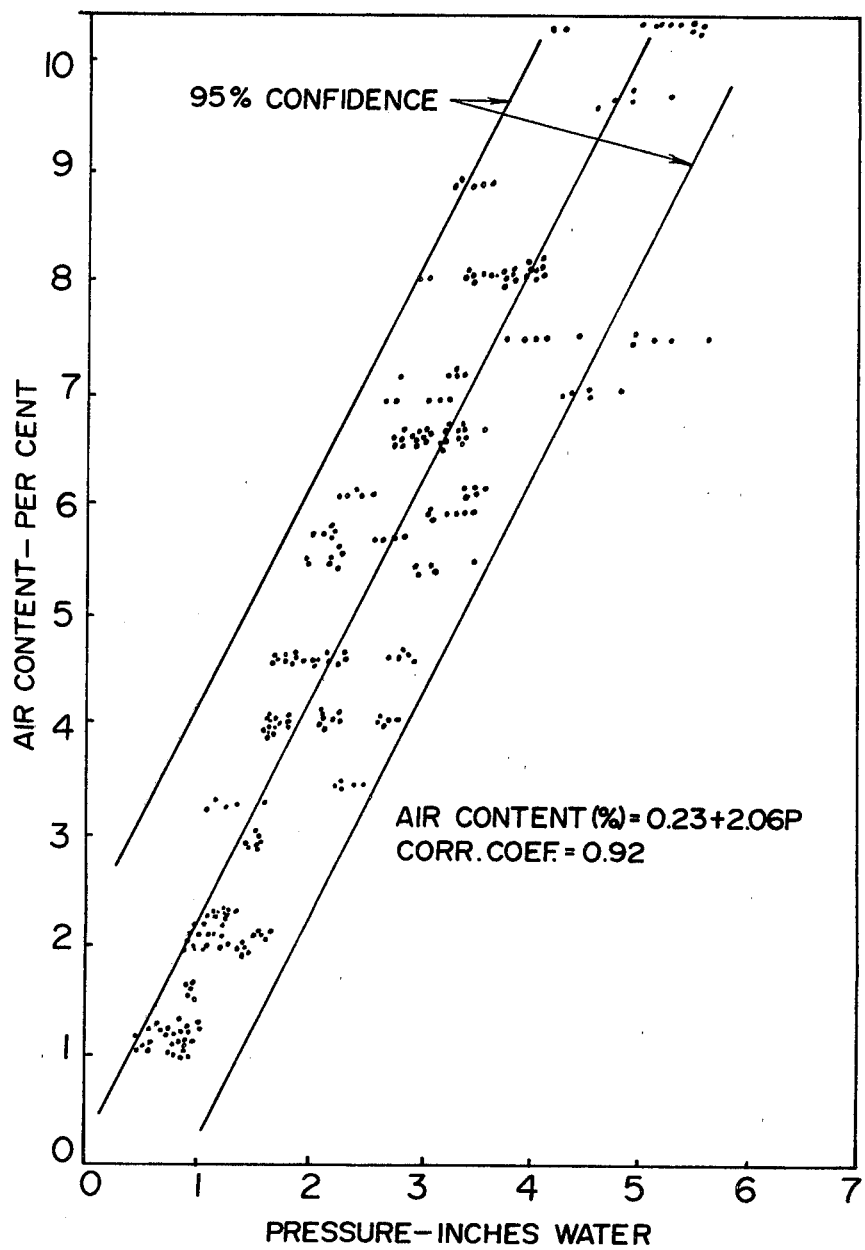
FIG. 4 shows graphically results obtained from tests detailed in the Example.

A variety of concrete mixes were prepared and tested. The mixes included various aggregate/cement ratios and water/cement ratios which were tested with different air contents as determined by the standard pressure test (C.S.A. and A.S.T.M.). Aggregate/cement ratios varied from 5/1 to 9/1 and water/cement ratios varies from 0.4/1 to 0.6/1. Some of the mixes also included the use of pozzolith admixture. The results are shown graphically on FIG. 4. Using linear regression, the equation for air content $(\%) = 0.23 + 2.06 \times$ Pressure (inches water). The correlation coefficient was 0.92.

I claim:

1. A method for indicating the air content of fresh concrete in situ, comprising;
providing a chamber having an open end and an opposite closeable end, said chamber provided with heating means and pressure measuring means;
inserting the open end of the chamber into the concrete, with opposite end opened;
closing said opposite end and heating the contents of the chamber with a predetermined energy input at a temperature less than the boiling point, and
determining the pressure increase in the chamber, wherein the pressure increase is a function of the air content.

2. An apparatus for determining the air content of fresh concrete in situ, comprising:
a chamber having an open end and an opposite sealable end having opening means, said open end adapted for insertion into fresh concrete;
heating means disposed in the chamber for heating the contents of the chamber; and
pressure measuring means for connection with the chamber for indicating a pressure increase in the chamber as the result of heating.

3. The apparatus of claim 2 having a removable top for the sealable end defining said opening means.

4. The apparatus of claim 2 including weighting means associated with said chamber to oppose lifting forces due to the pressure increase.

* * * * *